United States Patent [19]

Bramati et al.

[11] Patent Number: 5,981,433
[45] Date of Patent: *Nov. 9, 1999

[54] LIGNOSULFONATE/ETHOXYLATED POLY (1-PHENYLETHYL)PHENOL DISPERSING AGENTS AND AGROCHEMICALS COMPRISED THEREOF

[75] Inventors: Valerio Bramati, Arese, Italy; Isabelle Gubelmann-Bonneau, Paris, France; Antonio Marchetto, Saronno, Italy; Norman R. Pallas, Cranbury, N.J.

[73] Assignee: Rhone-Poulenc Chimier, Courbevoie Cedex, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/577,176

[22] Filed: Dec. 22, 1995

Related U.S. Application Data

[63] Continuation-in-part of application No. 08/574,331, Dec. 18, 1995, abandoned, which is a continuation of application No. 08/496,317, Jun. 29, 1995, abandoned.

[51] Int. Cl.$^6$ .......................... A01N 25/30; B01F 17/12; B01F 17/42
[52] U.S. Cl. .......................... 504/116; 504/330; 516/200
[58] Field of Search .................................. 504/116, 330; 71/DIG. 1; 252/353; 516/200

[56] References Cited

U.S. PATENT DOCUMENTS

| | | | |
|---|---|---|---|
| 2,858,250 | 10/1958 | Geary | 71/DIG. 1 |
| 3,737,551 | 6/1973 | Karsten et al. | 424/286 |
| 3,986,979 | 10/1976 | Moorer et al. | 252/353 |
| 4,310,520 | 1/1982 | Narazaki | 71/DIG. 1 |
| 4,389,238 | 6/1983 | Kaufman | 71/115 |
| 4,943,390 | 7/1990 | Hayes et al. | 252/355 |
| 5,045,109 | 9/1991 | Nakamura et al. | 71/DIG. 1 |
| 5,082,591 | 1/1992 | Marchetto et al. | 252/351 |
| 5,092,918 | 3/1992 | Kuchikata | 71/DIG. 1 |
| 5,180,416 | 1/1993 | Katou et al. | 71/DIG. 1 |
| 5,254,344 | 10/1993 | Dookhith et al. | 71/DIG. 1 |

FOREIGN PATENT DOCUMENTS

| | | |
|---|---|---|
| 0 201 417 | 11/1986 | European Pat. Off. . |
| 0 488 660 A1 | 6/1992 | European Pat. Off. . |
| 0 522 906 A1 | 1/1993 | European Pat. Off. . |
| 2 524 261 | 10/1983 | France . |
| 1 399 005 | 6/1975 | United Kingdom . |
| 2 238 960 | 6/1991 | United Kingdom . |

OTHER PUBLICATIONS

Search Report, Apr. 1995.

*Primary Examiner*—S. Mark Clardy
*Attorney, Agent, or Firm*—Burns, Doane, Swecker & Mathis, L.L.P.

[57] ABSTRACT

Dispersing agents for solid plant-protection agrochemicals, for example pesticidal dispersible granules, comprise (a) at least one alkali or alkaline earth metal or ammonium lignosulfonate, intimately admixed with (b) at least one optionally sulfated, ethoxylated or ethoxylated-propoxylated di- or tri(1-phenylethyl)phenol.

28 Claims, No Drawings

LIGNOSULFONATE/ETHOXYLATED POLY (1-PHENYLETHYL)PHENOL DISPERSING AGENTS AND AGROCHEMICALS COMPRISED THEREOF

CROSS-REFERENCE TO RELATED APPLICATIONS

This application is a CIP of application Ser. No. 08/574,331, filed Dec. 18, 1995, now abandoned, which is a continuation of application Ser. No. 08/496,317, filed Jun. 29, 1995, now abandoned.

BACKGROUND OF THE INVENTION

1. Technical Field of the Invention

The present invention relates to novel dispersing agents for solid plant-protection formulations, for the preparation of dispersible plant-protection granules and to said granules themselves.

2. Description of the Prior Art

Solid plant-protection formulations, namely, "wettable powders" and "dispersible granules," are agrochemicals currently being widely developed because they avoid the use of potentially toxic solvents and may be sealed in packaging which is conveniently recyclable, or in water-soluble sachets. The applicator or user thereof is thus better protected.

Other than the plant-protection active agent, these solid formulations include dispersing agents, binders and wetting and disintegrating agents. Such formulations are typically prepared by pregrinding the solid active agent(s) with the various solid additives, and then converting same, by adding water thereto, into a concentrated dispersion which is subsequently agglomerated in a pan agglomerator or in a turbosphere, or which is extruded prior to being dried via fluidized bed technique, or which can be spray-dried.

To date, the dispersing agents employed therefor must be solid; these are characteristically polymers such as ligno-sulfonates (sodium, calcium or ammonium salts), maleic anhydride/isobutylene copolymers (sodium or ammonium salts), condensed phenylsulfonic acids (sodium salts) or condensed naphthalenesulfonate/formaldehyde polymers (sodium or ammonium salts).

The aforesaid restriction is due to the requirements of the processing, which does not permit the addition of a liquid additive, unless a premix in water is desired which will subsequently be employed for the granulation.

Consequently, surface-active agents (surfactants) which are liquid or viscous at ambient temperature, such as ethoxy-lated alkylphenols or ethoxylated di- or tristyrylphenols, conventionally employed as dispersing agents in liquid formulations (in particular in microemulsions, concentrated emulsions, emulsifiable concentrates or concentrated suspensions), in this instance cannot be used. Furthermore, when these materials are evaluated in solid formulations, in particular in "dispersible granules," it is found that, besides the fact that they are difficult to process, they are not good dispersants, i.e., they produce granules which have a mediocre dispersibility and suspensivity.

SUMMARY OF THE INVENTION

It has now unexpectedly been determined that combinatory immixture of a lignosulfonate and of certain optionally sulfated, ethoxylated or ethoxylated-propoxylated di- or tristyrylphenols is well suited as a dispersing agent for solid plant-protection formulations.

Indeed, such admixture of these two classes of dispersants exhibits dispersing properties, in respect of a wide variety of active agents, which are far and synergistically superior to those of certain lignosulfonate used alone, and at least close to those of effective, but quite costly, dispersing polymers.

Briefly, the present invention features dispersing agents for solid plant-protection formulations, comprising:

(a) at least one alkali or alkaline earth metal or ammonium lignosulfonate [constituent (a)], and (b) at least one optionally sulfated, ethoxylated or ethoxylated-propoxylated di- or tri(1-phenylethyl)-phenol.

DETAILED DESCRIPTION OF BEST MODE AND PREFERRED EMBODIMENTS OF THE INVENTION

More particularly according to the present invention, the subject dispersing agent admixtures may be prepared by intimately mixing the constituents thereof.

It is very particularly advantageous to provide this admixture in a handlable solid form, especially in the form of a pourable or free-flowing powder. One technique for obtaining such a powder is to spray-dry an aqueous solution containing the two constituents (a) and (b).

The present invention thus also features, more particularly, a dispersing agent in powder form, prepared by spray-drying an aqueous solution comprising:

(a) at least one alkali or alkaline earth metal or ammonium lignosulfonate [constituent (a)], and (b) at least one optionally sulfated, ethoxylated or ethoxylated-propoxylated di- or tri(1-phenylethyl)-phenol which comprises from 7 to 40, alternatively 7 to 30, more preferably 7 to 20, oxyethylene or oxypropylene recurring structural units [constituent (b)]. The preferred weight ratio of the constituent (a)/constituent (b) being on the order to 95/5 to 50/50, preferably on the order of 95/5 to 70/30, in an amount corresponding to approximately 40 to 60 parts by weight of water per 100 parts by weight of the admixture of the aforesaid two constituents.

The totally sulfated constituents (b) are also within the ambit of the present invention.

Exemplary constituents (a) are Na, K, Ca, Mg and $NH_4$ lignosulfonates and, very particularly, that of Na and Ca.

Exemplary constituents (b) include:

(i) ethoxylated di(1-phenylethyl)phenol containing 10 oxyethylene recurring structural units, (ii) ethoxylated di(1-phenylethyl)phenol containing 7 oxyethylene recurring structural units, (iii) sulfated ethoxylated di(1-phenylethyl)phenol containing 7 oxyethylene recurring structural units, (iv) ethoxylated tri(1-phenylethyl)phenol containing 8 oxyethylene recurring structural units, (v) ethoxylated tri(1-phenylethyl)phenol containing 16 oxyethylene recurring structural units, (vi) sulfated ethoxylated tri(1-phenylethyl)-phenol containing 16 oxyethylene recurring structural units, Preferred constituents (b) include alkoxylated alkyl phenol compounds (e.g., Antarox 724P available from Rhône-Poulenc). Also preferred constituents (b) are alkoxylated tristyryl phenol compounds (e.g., Soprophor 796P available from Rhône-Poulenc). Also preferred are EO PO copolymers such as -[2,4,6-tris[1-(phenyl)ethyl]phenyl]-Ω-hydroxy poly (oxyethylene) poly (oxypropylene) copolymers. The preferred poly oxypropylene content averages 2–8 moles and the preferred polyoxy-ethylene content averages 16–30 moles.

An exemplary combination of constituents (a) and (b) includes a lignosulfonate calcium salt (e.g., Bretax available from Burgo) with a neutralized di- or tri-ethoxylated sulfated ammonium salt (e.g. Soprophor 4D384 available from Rhône-Poulenc) in a 9:1 ratio. The ammonium salt is desirably neutralized with diethanolamine.

Another exemplary combination of constituents (a) and (b) includes a sodium lignosulfonate (e.g., REAX 88B or Polyfon O available from Westvaco) with a di- or tristyrylethoxylated sulfated ammonium salt (e.g., Soprophor 4D384 available from Rhône-Poulenc) in a 7:3 ratio. Soprophor 4D384 is an ethoxylated tri-styryl phenol ammonium sulfate with 16 moles oxyethylene. The pH may be adjusted to about 6.0 before co-spray drying the materials.

The spraying operation may be carried out in a sprayer according to techniques which are well known to this art; the inlet air temperature is generally about 150°–300° C., and that at the outlet approximately 80°–100° C.

The dispersing agent according to the invention is very particularly well suited for the formulation of pesticide (herbicide, insecticide, fungicide) granules, since it is preferably in the form of a flowable powder.

This invention, thus, also features solid plant-protection formulations, especially in granule form, based on a solid plant-protection active agent and the dispersing agent described above.

Said solid plant-protection formulations advantageously comprise:

(1) 0.01% to 90%, preferably 40% to 90% by weight of a plant-protection active agent,
(2) 0.1% to 20% by weight of the dispersing agent according to the invention,
(3) 0% to 10% by weight of a disintegrating and/or binding agent,
(4) 0% to 10% by weight of an anticlotting agent,
(5) 0% to 10% by weight of a chemical stabilizing agent,
(6) 0% to 50% by weight of inert filler material relative to the total weight of the solid formulation, and
(7) 0% to 5% by weight of a wetting agent.

The following are representative active agents or agrochemicals which may comprise the aforesaid plant-protection formulations:

| Diuron | Linuron | Neburon | Carbaryl |
|---|---|---|---|
| Atrazine | Ametryn | Carboxim | Fentin Acetate |
| Zirarn | Maneb | Zineb | Carbendazim |
| Chlorothalonil | Mamcozeb | Copper Oxychloride | |

Exemplary of the other constituents are:
(1) wetting agent: anionic compounds such as alkylnaphthalene sulfonates, alkylbenzenesulfonates, alkylsulfosuccinates, taurates, alkyl sulfates, etc., or nonionic compounds such as acetylenic diols, ethoxylated alkylphenols, and the like,
(2) disintegrating and/or binding agent: starch, crosslinked polyvinylpyrrolidones, microcrystalline cellulose, crosslinked sodium carboxymethyl cellulose, soya polysaccharides, ion exchange resins, ethylene oxide/propylene oxide copolymers, polyethoxylated alkylphenols, and the like,
(3) anticlotting agent: ammonium or sodium phosphates, sodium carbonate or bicarbonate, sodium acetate, sodium metasilicate, magnesium, zinc or calcium sulfates, magnesium hydroxide, calcium chloride, molecular sieves, sodium alkylsulfosuccinates, barium or calcium oxides, silica and the like,
(4) chemical stabilizing agent: alkaline earth or transition metal sulfates, sodium hexametaphosphate, calcium chloride, boric anhydride, and the like,
(5) inert fillers: clays, synthetic and diatomaceous silicas, calcium or magnesium silicates, titanium dioxide, aluminum, zinc or calcium oxides, calcium or magnesium carbonates, sodium, ammonium, calcium sulfates, carbon black, and the like.

The aforesaid formulations may be constituted, by mixing these constituents, grinding the mixture dry, agglomerating same by addition of water to the ground particles, extruding or granulating, and then drying the shaped articles in a fluidized bed until granules are obtained which have a residual moisture or water content on the order to 0.1% to 2% by weight.

To efficiently carry out the process of the invention, the agglomeration of the ground particles is conducted by adding from approximately 10% to 20% by weight of water, relative to the weight of the particles; the extrusion or granulation sequence is carried out using techniques which are well known to this art, for example extrusion through a die, a grid, etc., granulation employing a coater, a turbosphere, etc.

In order to further illustrate the present invention and the advantages thereof, the following specific examples are given, it being understood that same are intended only as illustrative and in nowise limitative.

EXAMPLE 1

Preparation of the Dispersing Agent
A mixture comprising:
(a) 90 parts by weight of calcium lignosulfonate, and
(b) 10 parts by weight of ethoxylated tri(1-phenylethyl) phenol containing 16 oxyethylene recurring structural units, was introduced into 100 parts of water.

The solution obtained was introduced into a sprayer and spray-dried at a rate of 5 l/h; the air temperature at the inlet to the sprayer was 300° C. and that at the outlet was on the order to 90°–100° C.

A flowable powder was thus obtained.
Preparation of the Plant-Protection Formulation:
A mixture was prepared, containing:

| (1) Ziram | 80% by weight |
|---|---|
| (2) Supragil WP ® | 2% by weight |

(wetting agent, sodium diisoproylnaphthalenesulfonate marketed by Rhône-Poulenc)

| (3) Dispersing agent | 10% by weight |
|---|---|

(prepared as above, lignosulfonate/tri(1-phenylethyl)phenol 16 EO (90/10))

| (4) Starch (disintegrating agent) | 8% by weight |
|---|---|

This mixture was ground dry in an air jet mill; particles of a size on the order to 10 to 20 μm were obtained.

The particles were next agglomerated using 18 parts of water per 100 parts of particles in a Lödige® apparatus (marketed by Lödige).

The agglomerates were then extruded through a 0.8 mm diameter die.

The granules were then dried in an Aeromatic® fluid bed (marketed by Niro) until a residual moisture content of 2% in the granules was attained.

Dispersibility:

5 g of granules were poured into a 250-ml test tube filled with water of hardness D (342 ppm according to CIPAC standard MT-18 described in Collaborative International Pesticides Analytical Council Handbook, Vol. 1, Ed. G.R.AW (1970).

The test tube was sealed with a ground-glass stopper and then repeatedly inverted until all of the granules disintegrated and dispersed. The number of inversions required was recorded.

The number of inversions was 5; the dispersibility was therefore good.

Suspensivity:

The suspensivity ratio of the granules in water D was determined according to CIPAC standard MT-15.

It was 100%.

EXAMPLE 2 (COMPARATIVE)

Granules were prepared according to the procedure of Example 1, but using 10% of calcium lignosulfonate by itself instead of 10% of the calcium lignosulfonate/tri(1-phenylethyl)phenol 16 EO (90/10) mixture.

The characteristics of the formulation were as follows:

(i) Dispersibility: good (5 inversions)
(ii) Suspensivity ratio: 50%.

EXAMPLE 3 (COMPARATIVE)

Granules were prepared according to the procedure of Example 1, but using 10% of sodium lignosulfonate by itself instead of 10% of the calcium lignosulfonate/tri(1-phenylethyl)phenol 16 EO (90/10) mixture.

The characteristics of the formulation were as follows:

(i) Dispersibility: good (5 inversions)
(ii) Suspensivity ratio: 67%

EXAMPLE 4 (COMPARATIVE)

Preparation of the Plant-Protection Formulation:

A mixture was prepared, containing:

| (1) Ziram | 80 parts by weight |
|---|---|
| (2) Sodium diisopropylnaphthalenesulfonate (wetting agent | 2 parts by weight | pylnaphthalenesulfonate (wetting agent)

| (3) Starch (disintegrating agent) | 8 parts by weight |
|---|---|

This mixture was ground dry in an air jet mill; particles of a size on the order of 10 to 20 $\mu$m were obtained.

After introduction of 10 parts by weight of tri(1-phenylethyl)phenol 16 EO as the only dispersing agent, the particles were agglomerated using 18 parts of water per 100 parts of particles in a Lödige® apparatus (marketed by Lödige).

The agglomerates were then extruded through a 0.8 mm diameter die.

The granules were then dried in an Aeromatic® fluid bed (marketed by Niro) until a residual moisture content of 2% in the granules was attained.

The characteristics of the formulation were as follows:

(i) Dispersibility: good (10 inversions)
(ii) Suspensivity ratio: 32%.

EXAMPLE 5

Preparation of the Dispersing Agent:

A mixture comprising:

(a) 90 parts by weight of calcium lignosulfonate, and
(b) 10 parts by weight of ethoxylated tri(1-phenylethyl) phenol containing 16 oxyethylene recurring structural units, was introduced into 100 parts of water.

The solution obtained was introduced into a sprayer and spray-dried at a rate of 5 1/h; the air temperature at the inlet to the sprayer was 300° C. and that at the outlet was on the order of 90°–100° C.

A flowable powder was obtained.

Preparation of the Plant-Protection Formulation:

A mixture was prepared, containing:

| (1) Diuron | 85% by weight |
|---|---|
| (2) Soprophor AS/860 ® | 5% by weight |

(wetting agent, ethoxylated $C_{10}$ fatty alcohol absorbed onto silica, marketed by Rhône-Poulenc)

| (3) Dispersing agent (prepared as above, lignosulfonate/tri(1-phenylethyl)phenol 16 EO (90/10) | 1000 by weight |
|---|---|

This mixture was ground dry in an air jet mill; particles of a size on the order of 10 to 20 $\mu$m were obtained.

The particles were then agglomerated using 18 parts of water per 100 parts of particles, in a Lödige® apparatus (marketed by Lödige).

The agglomerates were then extruded through a 0.8 mm diameter die.

The granules were then dried in an Aeromatic® fluid bed (marketed by Niro) until a residual moisture content of 2% in the granules was attained.

The characteristics of the formulation were as follows:

(i) Dispersibility: good (5 inversions)
(ii) Suspensivity ratio: 95%.

EXAMPLE 6 (COMPARATIVE)

Granules were prepared according to the procedure of Example 5, but using 10% of calcium lignosulfonate by itself instead of 10% of the calcium lignosulfonate/tri(1-phenylethyl)phenol 16 EO (90/10) mixture.

The characteristics of the formulation were as follows:

(i) Dispersibility: good (5 inversions)
(ii) Suspensivity ratio: 21%.

EXAMPLE 7 AND COMPARATIVE EXAMPLE 8

In these examples, the properties of a formulation according to the invention were compared to those of a formulation comprising an ethoxylated alkylphenol only.

The following compositions were prepared:

TABLE 1

| Composition | Example 7 according to the invention | Comparative Example 8 |
|---|---|---|
| DIURON (herbicide) | 84% | 84% |
| calcium lignosulfonate/ SOPROPHOR DSS-7N | 10% ratio 90/10 | |
| calcium lignosulfonate/ ethoxylated sulfated nonylphenol | — | 10% ratio 90/10 |
| ANTAROX BO/327 | 1% | 1% |
| fillers: | | |
| kaolin | 2% | 2% |
| starch | 3% | 3% |

The SOPROPHOR DSS-7N was an ethoxylated sulfated distyrylphenol, neutralized by triethanolamine, in the form of an ammonium salt.

The ethoxylated nonylphenol (30 OE) was sulfated and in the form of an ammonium salt.

ANTAROX BO/327 was a $C_9$–$C_{11}$ etho-propoxylated surfactant.

The lignosulfonate was a calcium salt (BRETAX®), of lignin type.

The suspensivity tests were determined according to the CIPAC MT-15 norm with water of hardness D.

The accelerated aging tests were determined according to the following procedure:

5 g of granules were poured into a test tube. The tube was further immersed and maintained in water at 70° C. for 2 hours.

The results obtained are reported in the following Table 2:

TABLE 2

| Test | Example 7 according to the invention | Comparative Example 8 |
|---|---|---|
| Initial suspensivity | 76% | 20% |
| Suspensivity after the accelerated aging test | 71% | 19% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dispersing agent comprising (a) at least one alkali or alkaline earth metal or ammonium lignosulfonate, admixed with (b) at least one optionally sulfated, ethoxylated di- or tri(1-phenylethyl)phenol which comprises at least 7 oxyethylene recurring structural units.

2. The dispersing agent comprising (a) at least one alkali or alkaline earth metal or ammonium lignosulfonate, admixed with (b) at least one sulfated, ethoxylated di-or tri(1-phenylethyl)phenol which comprises a plurality of oxyethylene recurring structural units.

3. The dispersing agent as defined by claim 2, said constituent (b) comprising a neutralized sulfated, ethoxylated di- or tri(1-phenylethyl)phenol.

4. The dispersing agent as defined by claim 3, said sulfated ethoxylated di- or tri(1-phenylethyl)phenol being in the form of an ammonium salt.

5. The dispersing agent as defined by claim 1, said constituent (a) comprising Na or Ca lignosulfonate.

6. The dispersing agent as defined by claim 1, comprising at least 5% by weight of said at least one optionally sulfated, ethoxylated di- or tri(1-phenylethyl)phenol.

7. The dispersing agent as defined by claim 1, comprising at most 95% by weight of said alkali or alkaline earth metal or ammonium lignosulfonate.

8. The dispersing agent as defined by claim 1, wherein the weight ratio constituent (a)/constituent (b) is at most 95/5.

9. The dispersing agent as defined by claim 8, said weight ratio constituent (a)/constituent (b) ranging from about 95/5 to 50/50.

10. The dispersing agent as defined by claim 9, said weight ratio constituent (a)/constituent (b) ranging from about 95/5 to 70/30.

11. The dispersing agent as defined by claim 10, said weight ratio constituent (a)/constituent (b) ranging from about 90/10 to 75/25.

12. A dispersing agent comprising (a) at least 70% by weight of at least one alkali or alkaline earth metal or ammonium lignosulfonate, admixed with (b) at least one optionally sulfated, ethoxylated di- or tri(1-phenylethyl) phenol which comprises a plurality of oxyethylene recurring structural units.

13. The dispersing agent as defined by claim 1, comprising at most 50% by weight of said at least one optionally sulfated ethoxylated di- or tri(1-phenylethyl)-phenol.

14. The dispersing agent as defined by claim 13, comprising at most 30% by weight of said at least one optionally sulfated ethoxylated di- or tri(1-phenylethyl)-phenol.

15. A dispersing agent, comprising (a) at least one alkali or alkaline earth metal or ammonium lignosulfonate, admixed with (b) at least one optionally sulfated, ethoxylated di- or tri(1-phenylethyl)phenol which comprises a plurality of oxyethylene recurring structural units and wherein said constituent (b) further comprises a plurality of oxypropylene structural units.

16. The dispersing agent as defined by claim 1, comprising from 7 to 30 oxyethylene recurring structural units.

17. The dispersing agent as defined by claim 16, comprising from 7 to 20 oxyethylene recurring structural units.

18. The dispersing agent as defined by claim 17, comprising a free-flowing powder.

19. A dispersing agent, comprising (a) at least one alkali or alkaline earth metal or ammonium lignosulfonate, admixed with (b) at least one optionally sulfated, ethoxylated di- or tri(1-phenylethyl)phenol which comprises a plurality of oxyethylene recurring structural units and wherein said constituent (b) is an oxyethylene-oxypropylene copolymer having a polyoxypropylene content averaging 7–8 moles and a polyoxyethylene content averaging 16–30 moles.

20. The dispersing agent as defined by claim 19, wherein said constituent (b) is an α-[2,4,6-tris[1-(phenyl)ethyl]phenyl]-Ω-hydroxy poly(oxyethylene) poly (oxypropylene) copolymer.

21. A dispersing agent suitable for agrochemical applications, comprising (a) at least one alkali or alkaline earth metal or ammonium lignosulfonate, admixed with (b) at least one optionally sulfated, ethoxylated di- or tri(1-phenylethyl)phenol containing oxyethylene recurring structural units, said admixture of lignosulfonate and phenol capable of providing a suspensivity ratio in water of 100% when used to prepare agglomerates containing ziram.

22. A dispersing agent suitable for agrochemical applications, comprising (a) at least one alkali or alkaline earth metal or ammonium lignosulfonate, admixed with (b) at least one optionally sulfated, ethoxylated di- or tri(1-phenylethyl)phenol containing oxyethylene recurring structural units, said admixture of lignosulfonate and phenol capable of providing a suspensivity ratio in water of 95% when used to prepare agglomerates containing diuron.

23. A solid plant-protection agrochemical comprising the dispersing agent as defined by claim 1.

24. The agrochemical as defined by claim 23, comprising a herbicide, insecticicde or fungicide.

25. The agrochemical as defined by claim 23, comprising granules or extrudates thereof.

26. The agrochemical as defined by claim 23, further comprising at least one agent selected from the group consisting of a wetting agent, disintegrating and/or binding agent, anticlotting agent, chemical stabilizer, inert filler material, or mixture thereof.

27. A solid plant-protection agrochemical wherein the dispersing agent comprises (a) at least one alkali or alkaline earth metal or ammonium lignosulfonate, admixed with (b) at least one optionally sulfated, ethoxylated di- or tri(1-phenylethyl)phenol which comprises a plurality of oxyethylene recurring structural units, and wherein the agrochemical comprises at least one compound selected from the group consisting of diuron, atrazine, ziram, chlorothalonil, linuron, ametryn, maneb, neburon, carboxim, zineb, copper oxychloride, carbaryl, fentin acetate, carbendazine, mancozeb or mixture thereof.

28. A process for the preparation of the dispersing agent as defined by claim 1, comprising spray-drying an aqueous solution of said constituents (a) and (b).

* * * * *